US008557286B1

(12) United States Patent
Rein et al.

(10) Patent No.: US 8,557,286 B1
(45) Date of Patent: Oct. 15, 2013

(54) METHOD FOR PRODUCING A WATER-INSOLUBLE AMORPHOUS OR PARTIALLY AMORPHOUS CONTROLLED RELEASE MATRIX

(75) Inventors: Hubert Rein, Gießen-Wieseck (DE); Klaus-Jurgen Steffens, Rheibach/Flerzheim (DE)

(73) Assignee: EuroCeltique, S.A., Luxembourg (LU)

( * ) Notice: Subject to any disclaimer, the term of this patent is extended or adjusted under 35 U.S.C. 154(b) by 1072 days.

(21) Appl. No.: 09/980,727

(22) PCT Filed: Apr. 20, 2000

(86) PCT No.: PCT/EP00/03612
§ 371 (c)(1),
(2), (4) Date: Jul. 8, 2002

(87) PCT Pub. No.: WO00/64415
PCT Pub. Date: Nov. 2, 2000

(51) Int. Cl.
*A61K 9/14* (2006.01)
(52) U.S. Cl.
USPC .......................... 424/484; 424/485; 424/488
(58) Field of Classification Search
USPC ......... 424/400, 451, 464, 468, 484, 488, 489, 424/499, 465
See application file for complete search history.

(56) References Cited

U.S. PATENT DOCUMENTS

| | | | |
|---|---|---|---|
| 2,738,303 A | 3/1956 | Blythe et al. ........................ 167/82 |
| 3,065,143 A | 11/1962 | Christenson et al. | |
| 3,652,589 A | 3/1972 | Flick et al. .......... 260/326.5 M |
| 3,714,350 A | 1/1973 | Gough .......................... 424/203 |
| 3,830,934 A | 8/1974 | Flick et al. ...................... 424/330 |
| 3,845,770 A | 11/1974 | Theeuwes et al. ............. 128/260 |
| 3,880,991 A | 4/1975 | Yolles .............................. 424/22 |
| 3,950,508 A | 4/1976 | Mony et al. ...................... 424/19 |
| 3,965,256 A | 6/1976 | Leslie .............................. 424/22 |
| 3,974,157 A | 8/1976 | Shetty et al. ............. 260/247.2 B |
| 4,013,784 A | 3/1977 | Speiser ............................ 424/19 |
| 4,076,798 A | 2/1978 | Casey et al. .................... 424/419 |
| 4,132,753 A | 1/1979 | Blichare et al. ................. 264/25 |
| 4,173,417 A | 11/1979 | Kruder .......................... 366/89 |
| 4,230,687 A | 10/1980 | Sair et al. ...................... 424/22 |
| 4,259,314 A | 3/1981 | Lowey ............................ 424/19 |
| 4,265,875 A | 5/1981 | Byrne et al. ...................... 424/19 |
| 4,280,971 A | 7/1981 | Wischniewski et al. ........ 264/15 |
| 4,292,300 A | 9/1981 | Byrne et al. ...................... 424/19 |
| 4,310,483 A | 1/1982 | Dorfel et al. ................... 264/117 |
| 4,343,789 A | 8/1982 | Kawata et al. ................. 424/461 |
| 4,344,431 A | 8/1982 | Yolles ............................ 128/260 |
| 4,346,709 A | 8/1982 | Schmitt ........................ 128/260 |
| 4,366,172 A | 12/1982 | Lednicer ........................ 424/330 |
| 4,374,082 A | 2/1983 | Hochschild .................... 264/129 |
| 4,380,534 A | 4/1983 | Fukui et al. ...................... 264/38 |
| 4,389,393 A | 6/1983 | Schor et al. ...................... 424/19 |
| 4,406,883 A | 9/1983 | Byrne et al. ...................... 424/80 |
| 4,421,736 A | 12/1983 | Walters et al. .................... 424/21 |
| 4,483,847 A | 11/1984 | Augart ............................ 424/22 |
| 4,533,562 A | 8/1985 | Ikegami et al. .................... 427/3 |
| 4,612,009 A | 9/1986 | Drobnik et al. .............. 604/891 |
| 4,613,619 A | 9/1986 | Sleigh et al. .................. 514/546 |
| 4,621,114 A | 11/1986 | Watanabe ...................... 524/451 |
| 4,649,042 A | 3/1987 | Davis et al. .................... 424/438 |
| 4,720,384 A | 1/1988 | DiLuccio et al. .............. 424/78 |
| 4,762,220 A | 8/1988 | Lütke ............................ 198/519 |
| 4,764,378 A | 8/1988 | Keith et al. .................... 424/435 |
| 4,778,676 A | 10/1988 | Yang et al. ...................... 424/79 |
| 4,801,458 A | 1/1989 | Hidaka et al. ................. 424/443 |
| 4,801,460 A | 1/1989 | Goertz et al. ................. 424/465 |
| 4,806,337 A | 2/1989 | Snipes et al. ...................... 71/65 |
| 4,818,450 A | 4/1989 | Hall et al. ...................... 264/39 |
| 4,828,836 A | 5/1989 | Elger et al. .................... 424/419 |

(Continued)

FOREIGN PATENT DOCUMENTS

| | | |
|---|---|---|
| AU | 57224 | 5/1986 |
| AU | 8976091 A | 6/1992 |

(Continued)

OTHER PUBLICATIONS

Nicolas Follonier 1, Eric Doelker and Ewart T. Cole, *Evaluation of Hot-Melt Extrusion as a New Technique for the Production of Polymer-Based Pellets for Sustained Release Capsules containing high loadings of freely soluble drugs*, Drug Development and Industrial Pharmacy, 20(8), 1323-1339 (1994).

Nicolas Follonier, Eric Doelker and Ewart T. Cola[2], *Hot-Melt Extruded Pellets for the Sustained Release of Highly Dosed Freely Solluble Drugs*, Proceed. Intern. Symp. COntrol. Rel. Bioact. Mater., 18(1991), pp. 578-579.

*Twin Screw Extrusion in the Production of Novel Dosage Forms*, Pharmaceutical Manufacturing Review (Jun. 1994).

Follonier, Nicolas, et al., "Hot-Melt Extruded Pellets for the Sustained Release of Highly Dosed Freely Soluble Drugs", *Capsule News*, vol. 1, No. 3, Edited by Roland Daumesnil, (Jun./Jul. 1991).

Frank W. Goodhart et al., Design and Use of a Laboratory Extruder for Pharmaceutical Granulations, Journal of Pharm. Scien., 62(1), p. 133-136 (Jan. 1973).

(Continued)

*Primary Examiner* — James Rogers
(74) *Attorney, Agent, or Firm* — Jones Day (57) ABSTRACT

The invention relates to a method for producing pharmaceutical forms or preliminary stages thereof by means of extrusion. The pharmaceutical form has a matrix which the active agent is contained essentially, and whose essential characteristics are determined by the extrusion process and which comprises a polysaccharide and/or derivative thereof and/or a complex thereof and/or any mixture of the aforementioned substances with other substances and/or saccharides and/or derivatives thereof as an essential constituent, and at least one pharmaceutically active substance. The invention also relates to a pharmaceutical form which has a matrix in which the active agent is contained essentially, and whose essential characteristics are determined by the extrusion process, and which comprises a polysaccharide and/or derivative thereof and/or a complex thereof and/or any mixture of the aforementioned substances with other substances and/or saccharides and/or derivatives thereof as an essential constituent, and at least one pharmaceutically active substance. Finally, the invention also relates to the use of said pharmaceutical form for producing granulates for tabletting and filling capsules, for further processing using injection molding techniques and as an auxiliary material for direct tabletting and/or for producing monobloc pharmaceutical forms.

20 Claims, 6 Drawing Sheets

(56) References Cited

U.S. PATENT DOCUMENTS

| | | | |
|---|---|---|---|
| 4,834,984 A | 5/1989 | Goldie et al. | 424/488 |
| 4,842,761 A | 6/1989 | Rutherford | 252/90 |
| 4,844,907 A | 7/1989 | Elger et al. | 424/465 |
| 4,844,909 A | 7/1989 | Goldie et al. | 424/480 |
| 4,861,598 A | 8/1989 | Oshlack | 424/468 |
| RE33,093 E | 10/1989 | Schiraldi et al. | 424/876 |
| 4,879,108 A | 11/1989 | Yang et al. | 424/440 |
| 4,880,585 A | 11/1989 | Klimesch et al. | 264/141 |
| 4,880,830 A | 11/1989 | Rhodes | 424/470 |
| 4,882,151 A | 11/1989 | Yang et al. | 424/440 |
| 4,882,152 A | 11/1989 | Yang et al. | 424/440 |
| 4,882,153 A | 11/1989 | Yang et al. | 424/440 |
| 4,882,155 A | 11/1989 | Yang et al. | 424/440 |
| 4,882,156 A | 11/1989 | Yang et al. | 424/440 |
| 4,882,157 A | 11/1989 | Yang et al. | 424/440 |
| 4,882,159 A | 11/1989 | Yang et al. | 424/440 |
| 4,882,167 A | 11/1989 | Jang | 424/468 |
| 4,894,234 A | 1/1990 | Sharma et al. | 424/440 |
| 4,917,899 A | 4/1990 | Geoghegan et al. | 424/19 |
| 4,925,675 A | 5/1990 | Giannini et al. | 424/78 |
| 4,935,246 A | 6/1990 | Ahrens | 424/490 |
| 4,957,681 A | 9/1990 | Klimesch et al. | 264/211.23 |
| 4,959,208 A | 9/1990 | Chakrabarti et al. | 424/78 |
| 4,967,486 A | 11/1990 | Doelling | 34/1 |
| 4,970,075 A | 11/1990 | Oshlack | 424/451 |
| 4,975,284 A | 12/1990 | Stead et al. | 424/497 |
| 4,987,136 A | 1/1991 | Kreek et al. | |
| 4,990,341 A | 2/1991 | Goldie et al. | 424/484 |
| 4,992,100 A | 2/1991 | Koepff et al. | 106/125 S |
| 4,994,227 A | 2/1991 | Dietz et al. | 264/328.16 |
| 5,007,790 A | 4/1991 | Shell | 424/451 |
| 5,013,306 A | 5/1991 | Solomon et al. | 604/265 |
| 5,023,089 A | 6/1991 | Sakamoto et al. | 424/502 |
| 5,026,560 A | 6/1991 | Makino et al. | 424/494 |
| 5,030,400 A | 7/1991 | Danielsen et al. | 264/101 |
| 5,035,509 A | 7/1991 | Kruder | 366/89 |
| 5,049,394 A | 9/1991 | Howard et al. | 424/490 |
| 5,055,307 A | 10/1991 | Tsuru et al. | 424/693 |
| 5,073,379 A | 12/1991 | Klimesch et al. | |
| 5,102,668 A | 4/1992 | Eichel et al. | 424/490 |
| 5,126,145 A | 6/1992 | Evenstad | 424/465 |
| 5,132,142 A | 7/1992 | Jones et al. | 427/196 |
| 5,133,974 A | 7/1992 | Paradissis et al. | 424/480 |
| 5,147,593 A | 9/1992 | Huttllin | 264/500 |
| 5,162,117 A | 11/1992 | Stupak et al. | 424/475 |
| 5,165,952 A | 11/1992 | Solomon et al. | 427/2 |
| 5,167,964 A | 12/1992 | Muhammed et al. | 424/482 |
| 5,169,645 A | 12/1992 | Shukla et al. | 424/499 |
| 5,178,868 A | 1/1993 | Malmqvist-Granlund et al. | 424/490 |
| 5,183,690 A | 2/1993 | Carr et al. | 427/213.31 |
| 5,196,203 A | 3/1993 | Boehm | 424/490 |
| 5,202,128 A | 4/1993 | Morella et al. | 424/469 |
| 5,204,119 A | 4/1993 | Shiobara et al. | 424/489 |
| 5,229,148 A | 7/1993 | Copper | 426/5 |
| 5,234,697 A | 8/1993 | Sipos | 424/490 |
| 5,240,400 A | 8/1993 | Fujimoto et al. | 425/310 |
| 5,262,172 A | 11/1993 | Sipos | 424/490 |
| 5,266,331 A | 11/1993 | Oshlack et al. | 424/468 |
| 5,271,934 A | 12/1993 | Goldberg et al. | 424/401 |
| 5,273,758 A | 12/1993 | Royce | 424/465 |
| 5,283,065 A | 2/1994 | Doyon et al. | 424/467 |
| 5,290,560 A | 3/1994 | Autant et al. | 424/438 |
| 5,292,461 A | 3/1994 | Juch et al. | 264/37 |
| 5,296,266 A | 3/1994 | Kunugi et al. | 427/213 |
| 5,300,300 A | 4/1994 | Egidio et al. | 424/456 |
| 5,340,581 A | 8/1994 | Tseng et al. | 424/401 |
| 5,350,584 A | 9/1994 | McClelland et al. | 424/501 |
| 5,354,856 A | 10/1994 | Kawashima et al. | 536/127 |
| 5,356,635 A | 10/1994 | Raman et al. | 424/484 |
| 5,378,462 A | 1/1995 | Boedecker et al. | 424/94.29 |
| 5,380,535 A | 1/1995 | Geyer et al. | 424/484 |
| 5,395,626 A | 3/1995 | Kotwal et al. | 424/472 |
| 5,403,593 A | 4/1995 | Royce | 424/489 |
| 5,443,846 A | 8/1995 | Yoshioka et al. | 424/498 |
| 5,451,424 A | 9/1995 | Solomon et al. | 427/2.1 |
| 5,453,283 A | 9/1995 | Münch et al. | 424/489 |
| 5,456,923 A | 10/1995 | Nakamichi et al. | 424/489 |
| 5,472,710 A | 12/1995 | Klokkers-Bethke et al. | 424/468 |
| 5,476,528 A | 12/1995 | Trimm et al. | 71/21 |
| 5,478,577 A | 12/1995 | Sackler et al. | |
| 5,510,114 A | 4/1996 | Borella et al. | 424/452 |
| 5,516,205 A | 5/1996 | Oda et al. | 366/75 |
| 5,552,159 A | 9/1996 | Mueller et al. | 424/464 |
| 5,567,439 A | 10/1996 | Myers et al. | 424/486 |
| 5,700,410 A | 12/1997 | Nakamichi et al. | 264/122 |
| 5,958,452 A | 9/1999 | Oshlack et al. | 424/457 |
| 6,261,599 B1 | 7/2001 | Oshlack et al. | 424/457 |
| 6,323,265 B1 | 11/2001 | Bengs et al. | |
| 6,335,033 B2 | 1/2002 | Oshlack et al. | 424/457 |

FOREIGN PATENT DOCUMENTS

| | | |
|---|---|---|
| CA | 2082573 | 5/1993 |
| CA | 2131350 A1 | 3/1995 |
| CA | 2150304 A1 | 12/1995 |
| CA | 2343946 | 11/1999 |
| DE | 2439538 | 3/1976 |
| DE | 3602370 A1 | 8/1987 |
| DE | 3623193 A1 | 1/1988 |
| DE | 4329794 A1 | 3/1995 |
| EA | 0624366 B1 | 11/1994 |
| EP | 0032004 A | 12/1980 |
| EP | 0097523 A2 | 1/1984 |
| EP | 0043254 B1 | 5/1984 |
| EP | 0108218 A2 | 5/1984 |
| EP | 0118240 A2 | 9/1984 |
| EP | 0147780 A2 | 12/1984 |
| EP | 0152379 A2 | 8/1985 |
| EP | 0189861 A2 | 8/1986 |
| EP | 204596 | 12/1986 |
| EP | 0208144 A1 | 1/1987 |
| EP | 0214735 A2 | 3/1987 |
| EP | 0241615 B1 | 10/1987 |
| EP | 0248548 A2 | 12/1987 |
| EP | 0249347 A2 | 12/1987 |
| EP | 0249347 B1 | 12/1987 |
| EP | 0251459 A2 | 1/1988 |
| EP | 0253104 A1 | 1/1988 |
| EP | 0254978 A1 | 2/1988 |
| EP | 0256127 B1 | 2/1988 |
| EP | 0267702 A2 | 5/1988 |
| EP | 0271193 A2 | 6/1988 |
| EP | 0275834 A1 | 7/1988 |
| EP | 0295212 A2 | 12/1988 |
| EP | 0327295 A2 | 8/1989 |
| EP | 0338383 B1 | 10/1989 |
| EP | 0068450 B1 | 1/1990 |
| EP | 0351580 A2 | 1/1990 |
| EP | 0377518 A2 | 1/1990 |
| EP | 0361910 A1 | 4/1990 |
| EP | 03610680 B1 | 4/1990 |
| EP | 0368247 A2 | 5/1990 |
| EP | 0375063 A1 | 6/1990 |
| EP | 0377517 A2 | 7/1990 |
| EP | 0415693 A1 | 3/1991 |
| EP | 0459 819 A2 | 5/1991 |
| EP | 0430287 B1 | 6/1991 |
| EP | 0452145 A2 | 10/1991 |
| EP | 0239983 B1 | 11/1991 |
| EP | 0463833 A2 | 1/1992 |
| EP | 0481600 | 4/1992 |
| EP | 0320480 B1 | 11/1992 |
| EP | 0526862 A1 | 2/1993 |
| EP | 0529396 | 3/1993 |
| EP | 0531611 A1 | 3/1993 |
| EP | 0533297 A1 | 3/1993 |
| EP | 0534628 A1 | 3/1993 |
| EP | 0535841 A1 | 4/1993 |
| EP | 0544144 A1 | 6/1993 |
| EP | 0546676 A1 | 6/1993 |
| EP | 0677065 A1 | 8/1993 |
| EP | 665010 A1 | 10/1993 |
| EP | 0574894 A1 | 12/1993 |

(56) References Cited

FOREIGN PATENT DOCUMENTS

| | | |
|---|---|---|
| EP | 0580860 | 2/1994 |
| EP | 580860 A1 | 2/1994 |
| EP | 0582380 A1 | 2/1994 |
| EP | 0595311 A1 | 5/1994 |
| EP | 0609961 A1 | 8/1994 |
| EP | 0624366 B1 | 11/1994 |
| EP | 0636370 A1 | 2/1995 |
| EP | 0491238 B1 | 3/1995 |
| EP | 0642788 A2 | 3/1995 |
| EP | 0205282 B1 | 9/1995 |
| EP | 0459 819 B1 | 8/1996 |
| EP | 0118 240 B2 | 6/1997 |
| FR | 2273512 | 1/1976 |
| FR | 2273584 | 1/1976 |
| FR | 2642420 A1 | 8/1990 |
| GA | 2117239 A | 10/1983 |
| GB | 0997399 | 7/1965 |
| GB | 1405088 | 9/1975 |
| GB | 1504553 | 3/1978 |
| GB | 1513166 | 6/1978 |
| GB | 2030861 A | 4/1980 |
| GB | 2053681 B | 2/1981 |
| GB | 2111386 A | 7/1983 |
| GB | 2196848 A | 5/1988 |
| GB | 2207355 B | 1/1991 |
| GB | 2246514 A | 2/1992 |
| GB | 2281204 A | 3/1995 |
| GB | 2284760 A | 6/1995 |
| JP | 5257315 | 5/1977 |
| JP | 2223513 A | 9/1990 |
| JP | 2223533 A | 9/1990 |
| WO | 9104015 | 4/1991 |
| WO | 9119484 | 12/1991 |
| WO | 9119485 | 12/1991 |
| WO | 9201446 | 2/1992 |
| WO | 9202209 | 2/1992 |
| WO | 9205774 | 4/1992 |
| WO | 9206679 | 4/1992 |
| WO | 9215285 | 9/1992 |
| WO | WO 92/15285 * | 9/1992 |
| WO | WO9218106 | 10/1992 |
| WO | 9222283 | 12/1992 |
| WO | 9300063 A1 | 1/1993 |
| WO | 9300076 | 1/1993 |
| WO | 9304675 | 3/1993 |
| WO | 9307861 | 4/1993 |
| WO | WO9307859 | 4/1993 |
| WO | 9310765 A1 | 6/1993 |
| WO | 9317667 | 9/1993 |
| WO | WO9318753 | 9/1993 |
| WO | WO9324110 | 12/1993 |
| WO | 9403160 | 2/1994 |
| WO | 9403161 | 2/1994 |
| WO | 9405262 | 3/1994 |
| WO | WO9408568 | 4/1994 |
| WO | 9422431 | 10/1994 |
| WO | 9423700 | 10/1994 |
| WO | WO9423698 | 10/1994 |
| WO | 9514460 | 6/1995 |
| WO | 9810762 | 3/1998 |
| WO | WO 98/18610 | 5/1998 |
| WO | WO 99/02600 | 1/1999 |
| WO | WO 99/34780 | 7/1999 |
| WO | WO 00/29477 | 5/2000 |

OTHER PUBLICATIONS

Publication, KEX, Twin-Screw Compounding Extruder, (Oct. 1989).
Abstract No. 2-223533 "Agent with Release-Controlled Matrix".
Derwent Abstract DE 2553026 (1976).
Derwent Abstract of JP 62040277 (1987).
Derwent Abstract of JP58109411 (1983).
Derwent Abstract EP 358 107 (1990).
Sekiguchi, et al., "Studies on Absorption of Eutectic Mixture. . . ", Chem. Pharm. Bull., vol. 9 (1961), pp. 866-872.
A.R. Gennaro, "Particle Phenomena and Coarse Dispersions", Remington's Pharmaceutical Sciences, 17th Edition, 1985, p. 301.
J.L. Ford, "The Current Status of Solid Dispersions", Pharm. Acta Helv. 61, Nr. 3 (1986), pp. 69-88.
CA 74:67660(1996) (1 page).
CA 101:60081 (1996) (1 page).
CA 113:98975 (1996) (1 page).
CA 113:218240 (1996) (1 page).
CA 114:30199 (1996) (1 page).
CA 112:75438 (1996) (1 page).
CA 115:177364 (1997) (1 page).
R. Kinget, et al., "Preparation and Properties of Granulates Containing Solid Dispersions", Acta Phar. Tech., vol. 31, No. 2, 1985, pp. 57-62.
M.J. Jozwiakowski et al., "Characterization of a Hot-Melt Fluid Bed Coating Process for Fine Granules", Pharm. Research, vol. 7, No. 11, 1990, pp. 1119-1124.
B. Evrard et al., "Melt Granulation With a New Laboratory High-Shear Mixer", Laboratoire de Pharmacie Galenique, Institut de Pharmacie.
M. Niskanen et al., "Pelletization in a Centrifugal Granulator, Part I: Effects of Binder-Solution Concentration", Pharm. Tech. Int'l., Oct. 1990, pp. 22-38.
L. Lachman et al., "The Theory and Practice of Industrial Pharmacy", p. 315, Lea & Febiger, Phi. 1976.
FDA Guide to Inspections of Oral Solid Dosage Forms Pre/Post Approval Issues for Development and Validation, Jan. 1994.
T. Schaefer et al., "Melt Pelletization in a High Shear Mixer 1 Effects of Process Variables and Binder", Acta Pharm. Nord. vol. 4, No. 3, pp. 133-140, 1992.
T. Schaefer et al., "Melt Pelletization in a High Shear Mixer II Power Consumption and Granule Growth", Acta Pharm. Nord. vol. 4, No. 3, pp. 141-148, 1992.
T. Schaefer, et al., "Melt Granulation in a Laboratory Scale High Shear Mixer", Drug Dev. and Indust. Phar., vol. 16, No. 8, pp. 1249-1277, 1990.
McTaggart, C.M. et al., "The Evaluation of Formulation and Processing Conditions of a Melt Granulation Process", Int'l. J. Pharm. vol. 19, No. 2, issued 1984, pp. 139-148.
El-Shanawany, S., "Sustained Release of Nitrofurantion From Inert Wax Matrixes", J. Controlled Release, vol. 26, No. 1, issued 1993, pp. 11-19.
P. Flanders, et al., "The Control of Drug Releases From Conventional Melt Granulation Matrices", Drug Dev. and Industrial Pharm., vol. 13, No. 6, pp. 1001-1022, 1987.
Thomsen, L. Juul, "Matrix Pellets Prolonged Formulations Prepared by Melt Pelletization", Dept. of Pharm. Royal Danish School of Pharmacy, 1992.
Thomsen,L. Juul, et al., "Prolonged Release Matrix Pellets Prepared by Melt Pelletization I. Process Variables", Drug Development and Industrial Pharmac y, vol. 19, No. 15, pp. 1867-1887 (1993).
Thomsen, L. Juul, el al., "Prolonged Release Matrix Pellets Prepared by Melt Pelletization II. Hydrophobic Substances as Meltable Binders", Drug Development and Industrial Pharmacy, vol. 20, No. 7, pp. 1179-1197 (1994).
Thomsen, L. Juul, "Utilizing melt pelletization lequnique for the preparation of prolonged release products", Pelletization. (material elaborated by assistant Prof. Lars Juul Thomsen, Dept. of Pharmaceutics, Royal Danish School of Pharmacy for the DIE course "Pelletization Technology". Nov. 1992, 106 pages plus appendixes.
Thomsen, L. Juul, "Prolonged Release Matrix Pellets Prepared by Melt Pelletization. Part IV: Drug Content, Drug Particle Size and Binder Composition", Pharmaceutical Technology Europa, pp. 19-22 (Oct. 1994).
N. Follonier et al., "Evaluation of Hot-Melt Extrusion as a New Technique for the Production of Polymer-Based Pellets for Sustained Release Capsules Containing High Loadings of Freely Soluble Drugs", Drug. Dev. and Industr. Pharm., vol. 20, No. 8, pp. 1323-1339, (1994).
Sustained Release Medications, pp. 50-53 Noyes Data Corp.(J.C. Johnson), 1980.
M.A. Longer, "Sustained-Release Drug Deliver Systems", Remington's Pharm. Scie., 18th Edition, pp. 1676-1693, 1990.

(56) References Cited

OTHER PUBLICATIONS

M. Zahirul I. Khan, "Recent Trends and Progress in Sustained or Controlled Oral Delivery of Some Water Soluble Drugs: Morphine Salts, Diltiazem and Captopril", Drug Devl. and Indust. Pharm., vol. 21, No. 9, pp. 1037-1070, 1995.

J.P. Skelly, Scael-up of Immediate Releae Oral Solid Dosage Forms, AAPS/FDA Workshop Committee, Pharmaceutical Technology, pp. 68-74, Apr. 1995.

SK Baveja et al., Int. J. Pharmaceutics, 41, (1988), pp. 55-62.

Formulating for Controlled Release with METHOCEL® Premium Cellulose Ethers, The Dow Chemical Company, 1989.

M.S. Vazquez et al., Ddrug Dev. & Ind. Pharmacy, 18 (11 & 12), pp. 1355-1378 (1992).

L W S Cheong et al., Pharm. Res. 9 (11), pp. 1510-1514 (1992).

Hunt et al., Clin. Ther., vol. 13, No. 4. pp. 482-488, 1990.

METHOCEL, Colorcan. Technical Information.

DA Alderman, Int. J. Pharm. Tech. and Prod. Mfr., 5(3), pp. 1-9, 1984.

HE Huber et al., J. Pharm. Sci. 55 (9), Sep. 1966, pp. 974-978.

Lin SY et al., Current Therapeutic Research 52 (3), pp. 486-492, Sep. 1992.

Aqualon Technical Information Bulletin, VC-585, 1991.

P. Colombo, Advanced Drug Delivery Reviews, 11(1993), pp. 37-57.

KV Range Rao et al., Int. J. Pharmaceutics, 48 (1988), pp. 1-13.

JE Hogan, Drug Dev. & Ind. Pharmacy, 15 (8 & 7), p. 975-999, (1989).

JL ford et al., Int. J. Pharmaceutics, 24(1985), pp. 327-338.

PB Daly et al., Int. J. Pharmaceutics, 18 (1984), pp. 201-205.

E.M.G. van Bommel, "Production and Evaluation of In Vitro Release Characteristics of Spherical Grandient Matrix Systems", Acta Phar., Technol. 3b (2), pp. 74-78, 1990.

Nicolas Follonier et al., "Various Ways of Modulating the Release of Diltiazem Hydrochloride from Hot-melt Extruded Sustained Release Pellets Prepard Using Polymeric Materials", Journal of Controlled Release, 36, pp. 243-250 (1995).

Alan Royce et al., "Alternative Granulation Technique: Melt Granulation", Drug Development and Industrial Pharmacy, 22 (9 & 10), pp. 917-992 (1996).

Derwent Abstract of EP 0208144, published Jan. 14, 1987.

English translation of Japanese text of J.L. White, *Twin Screw Extrusion, Technology and Principles*, pp. 14 and 37, 1981.

EP 07 103 714.7 Search Report, Aug. 31, 2007.

* cited by examiner

METHOD FOR PRODUCING A WATER-INSOLUBLE AMORPHOUS OR PARTIALLY AMORPHOUS CONTROLLED RELEASE MATRIX

The invention relates to a method for producing pharmaceutical dosage forms or precursors thereof by means of extrusion.

The invention further relates to a pharmaceutical dosage form which may be produced by means of extrusion methods.

Extrusion is a widespread process, especially in the adhesive industry or in plastics processing for modifying polysaccharides, in particular starches. Extrusion is known in food technology for the production of starch-containing compositions, such as noodles, so-called peanut flips or various sweets. However, the production conditions of all of these products are selected in such a way that foamed, so-called popped products are obtained.

In pharmaceutical technology extrusion is used for the processing of waxes, fatty alcohols, fats and various thermoplastics and duroplastics. For example, extruded matrices from various polymer compounds are disclosed in EP-A2 0 240 904, EP-A2 0 240 906 and EP-A2 0 358 105. The processing of starch-containing mixtures into pharmaceutical products (capsules) by means of an injection-molding technique is described in EP-B2 0 118 240. In this context, it is not so well known how the polysaccharides used change during extrusion.

Extrusion methods for producing solid dispersions of an active agent in a polymeric carrier are known from EP-A 0 580 860. Among the raw materials which may be used are starch and starch derivatives mentioned in general. However, the method described therein is not suitable for preparations having starch as the main ingredient.

In pharmaceutical technology, orally administered dosage forms such as, for example, tablets, dragées or capsules are by far the most important. These also include the so-called controlled release (retard) dosage forms, which contain a relatively high dose of active agent and release this active agent in a controlled manner over a longer period of time. For the patient, this means that the frequency of medication can be significantly reduced. From a medical-pharmacological point of view, the advantage of the controlled release dosage forms lies in a very uniform concentration of the active agent in the blood, producing a long-lasting effect with less side effects. When formulating controlled release dosage forms, the so-called matrix form is of fundamental importance. Matrix means a shaped body, such as, for example, a tablet or dragée made of inert adjuvants, which release the active agents into the gastro-intestinal tract in a controlled manner. The release of the active agent generally occurs partly by diffusion, partly by slow degradation of the matrix.

In pharmaceutical technology such matrices are produced from synthetic polymers, such as polyacrylate or polyethylene. In this context, extrusion methods for the production of controlled-release forms from synthetic raw-materials are also known.

One fundamental disadvantage of dosage forms produced hitherto by means of extrusion methods is the use of excipients such as plastics, waxes or even fatty alcohols. These adjuvants, which are not biologically degradable and in part environmentally harmful, such as residual monomers in the polymers used, are even up to the present day indispensable for dosage forms produced by means of extrusion methods and allowing a controlled and slow release of the active agent.

Moreover, there is no known extrusion method for the production of dosage forms which allow a rapid release of the active agent.

There is thus a great need for the provision of an extrusion method for the production of dosage forms having regulated, i.e. by choice delayed or even a more rapid release of the active agent, which overcomes the disadvantages of the prior art, and which particularly avoids the use of biologically non-degradable and to some extent even environmentally toxic excipients. Further objects can be gathered from the following description of the invention.

The solution of the objects relating to the method lies in the combination of features of claim 1.

Advantageous embodiments of the inventive method are defined in the method sub-claims.

According to the invention a method for producing of dosage forms or precursors thereof by means of extrusion is suggested, characterized in that the dosage form has a matrix which essentially comprises the active agent content, the essential features of which matrix are formed by the extrusion, and which comprises a biologically degradable polysaccharide and/or a derivative thereof and/or a complex thereof and/or any mixture of the aforementioned substances with other substances and/or saccharides and/or derivatives thereof as a constituent of the matrix and at least one pharmaceutically effective substance.

According to a preferred embodiment, the release of the active agent of the dosage form is regulated by the addition of adjuvants and/or by variation of the extrusion process parameters, such as temperature, geometry of the dies and/or the extrusion speed.

In a further preferred embodiment the matrix of the dosage form made according to the invention is amorphous or partially amorphous.

Furthermore, the invention in a preferred embodiment relates to a method, wherein the dosage form according to the invention comprises in the matrix starch or a derivative thereof, in part-icular amorphous or partially amorphous starch or a derivative thereof, as the polysaccharide.

In a further preferred embodiment the invention relates to a method of production wherein the dosage form comprises a water-insoluble and preferably a swellable matrix.

According to an especially preferred embodiment, the dosage form according to the invention is a controlled release matrix.

Further preferred embodiments include a dosage form according to the invention showing a release of the active agent which essentially follows the lapidus function and which especially preferred shows a release of the active agent which is adjustable over 24 hours or longer.

A further essential object of the invention lies in the provision of a dosage form which essentially can function without biologically degradable ingredients.

According to the invention, this object is solved by a dosage form comprising a matrix in which the active agent is essentially contained, and whose essential properties are determined by the extrusion process and which comprises a polysaccharide and/or a derivative thereof and/or a complex thereof and/or any mixture of the aforementioned substances with other substances and/or saccharides and/or derivatives thereof as an essential constituent of the matrix, and at least one pharmaceutically effective substance.

Furthermore, the invention relates to the use of the inventive dosage form as adjuvant in direct tabletting, for producing granulates for tabletting and capsule-filling, for further processing using injection molding techniques and/or for producing mono-block pharmaceutical dosage forms.

During the extrusion process, i.e. while using or applying heat, shear forces and pressure, an amorphous or partially amorphous matrix is generated from the crystalline or partly crystalline polysaccharides, in particular from starch or derivatives thereof, or from mixtures of these components. For the reproducible production of dosage forms based on the extrusion of polysaccharides and derivatives thereof, the extrusion conditions, such as temperature, die geometry and extrusion speed, are very important. For example, native starch may be completed plastified or vitrified under suitable extrusion conditions, so that homogeneous plastic-like shaped bodies are obtained.

When extruding starch, heating is only necessary at the beginning of the process. In the further course of the process, the heat generated by the strong shear and friction is preferably eliminated by cooling, in order to maintain a constant temperature. The formulations used in the inventive method are comprised of a mixture of polysaccharides and/or derivatives thereof, preferably of a mixture of starch and/or starch derivatives, there being various types of starch which are suitable. Furthermore, the mixture contains at least one pharmaceutically effective substance in an amount of up to 50% and preferably of up to 30%, based on the total weight of the formulation, and may additionally comprise further different substances. Water in concentrations of up to 15% should be added to the thoroughly mixed dry formulation. Where a forced conveying extruder is used, a lesser water content than 15% is sufficient.

After thoroughly mixing and the addition of water the obtained pre-blend should preferably be screened so that it is free of lumps, in order to ensure perfect conveyance through the screw feeder. Starting and cleaning of the extruder may for example be carried out using corn grit. When generating a matrix according to the inventive method, the temperature at the orifice of the extruder should not exceed 100° C. under normal pressure, since at temperatures above 100° C. the formation of a matrix free of pores will hardly be possible. The total energy fed into the process, in the form of shear forces, temperature, heat or pressure, should be as constant as possible and should be sufficient to achieve glass transition. The optimal screw speed and geometry of dies may be adjusted to the mixture comprised of the inventive carrier and water. At extrusion temperatures below 100° C. and suitable screw speeds transparent and completely amorphous products are obtained in most cases. The degree of plastification of the active agent/polysaccharide mixture and preferably of the active agent/starch mixtures is closely linked to the screw speed. While extrusion is no longer possible below the lowest speed, a screw speed which is too high causes the dosage form to "pop open".

Varying the extrusion process parameters allows the production of dosage forms according to the inventive method which show regulated release of the active agent. Within the meaning of the present invention "regulated" means that by the inventive extrusion method dosage forms with rapid as well as dosage forms with delayed release, so-called controlled-release dosage forms with release periods of up to 24 hours or longer, may be produced. Besides the process parameters already mentioned, also the processing temperature is of major importance in relation to the regulation of the release of the active agent. Dosage forms with rapid release may be obtained for example by extrusion below the temperature of gelatinisation of the polysaccharides used in each case. Since, among other things the density of the matrix influences the release of the incorporated active agents, corresponding dosage forms with controlled release may be produced by partial to complete vitrification, i.e. by transition into the amorphous state of the polysaccharide-containing mixture under suitable extrusion conditions. In contrast to previously described systems, such an amorphous or partially amorphous matrix according to the inventive method, which preferably is made of amorphous or partially amorphous starch or derivatives thereof or of mixtures of these components, is essentially not water-soluble, but instead preferably swellable and water-insoluble. The pharmaceutically effective substance or substances may be present in the matrix in dissolved, solid or liquid form.

Examples of starches which may be used in the inventive production method are tapioca starch, wheat starch, potato starch, starch 1500® (partially pregelatinized corn starch, available from Colorcon), Waxylis® (wax corn starch from Roquette), Eurylon 7® (amylo corn starch available from Roquette), corn starch, acetylic starch.

In addition, dosage forms are obtainable according to the inventive extrusion method which have regulated release of the active agent due to the addition of adjuvants. For accelerating release of the active agent by formation of pores in the matrix, the following substances may be added, for example:

- hydrophilic or amphiphilic solids, water-soluble substances, such as sodium chloride, lactose, surface-active substances, such as for example sodium lauryl sulfate, silica (colloidally dispersed and/or as xerogel),
- hydrophilic or amphiphilic liquids, polyglycols, such as for example glycerol, polyethylene glycol, surface-active substances, such as for example polysorbate,
- gases, such as for example nitrogen, carbon dioxide.

A reduction in the release of the active agent by inhibiting the diffusion may for example be effected by the addition of the following adjuvants:

- lipophilic or amphiphilic adjuvants of natural, synthetic and/or partially synthetic origin, such as for example fats, fatty acids, waxes in solid or liquid state,
- saturated or unsaturated hydrocarbons,
- metal soaps, such as for example magnesium stearate.

Furthermore, a reduction in the release of the active agent may be achieved by the formation of stoichiometric or non-stoichiometric complexes, such as for example iodine-starch complex, miltefosin-amylose complex.

Moreover, the release of the incorporated active agents can be influenced by the use of suitable blends of the components of the matrix, preferably by using blends of different starches and/or derivatives thereof. Further factors which can also influence the release of the active agent are the outer surface of the shaped body of the dosage form and its particle size, or the distribution of the active agent(s) within the particle.

An examination of the course of the release of the active agent shows that the release of the active agent is preferably controlled by diffusion and follows the so-called lapidus rule, as shown in the tests described below. The course of the release does not change, even after storage of the dosage forms over several months.

The dosage forms produced according to the inventive method may be used to produce granulates for tabletting and filling capsules, may be used as adjuvants for direct tabletting, for further processing by means of extrusion molding techniques and/or as mono-block dosage forms, where the extrudate is formed by means of a suitable arrangement at the extrusion die—similar to the case of soap production. The inventive method allows the production and use of mono-block forms, in the process of which an extrude is created that is vitrified only at the surface and includes the active substance/carrier mixture in an unchanged state in its interior. In order to achieve the desired bio-pharmaceutical properties of the dosage form, all adjuvants known for producing solid forms may be used.

Drying of the dosage form can take place merely through the frictional heat that is created, so that a final drying step is not necessary. In a production extruder, preferably a twin screw extruder, especially preferred in a forced conveying twin screw extruder, all process steps, such as dosing, moistening, mixing, extruding and forming can be carried out continuously. The inventive method is thus able to combine the processes of mixing, granulating and drying, for which no additional energy has to be expended, in one piece of equipment.

According to the invention, also the number of possible incompatibilities is reduced, since the dosage form comprises for example only one excipient, preferably starch or a derivative thereof, and one pharmaceutically effective substance. The matrix made according to the inventive method further prevents a possible unintended demixing.

The following examples show that the degree of retardation of the active agent is best regulated by the process or the process parameters, the type of polysaccharide or the addition of further adjuvants. The examples serve to illustrate the invention only and do not represent any limitations to certain embodiments or applications. Rather, further embodiments within the scope defined by the attached claims are conceivable.

EXAMPLES

In the following examples, which have been carried out according to the inventive method, various polysaccharides with the addition of caffeine as a model active agent were used. The extrusion experiments were carried out with a Brabender one-screw extruder type 811201. This device has three segments which may be tempered independently of each other, the feed area, the screw area and the die. A conveyor screw was used without compression, having a screw length of 22 cm, a screw diameter of 19 mm, a core diameter of 16 mm and a pitch of 15 mm. Dies with different diameters between 2.5 and 7 mm were used.

The batch size in the experiments was between 350 and 600 grams. Active agent and starch were thoroughly mixed in a Stephan mixer, moistened with 15% water; this pre-blend was then screened until free of lumps.

Temperatures of about 65° C. in the feed area of the extruder, of about 80° C. in the screw area and of about 98° C. at the die have proven to be a suitable choice of temperature for carrying out the inventive method.

The proof of the transition of the crystalline or partially crystalline structures of the polysaccharides into amorphous or partially amorphous structures may be carried out with the aid of different techniques.

Figure 1A:
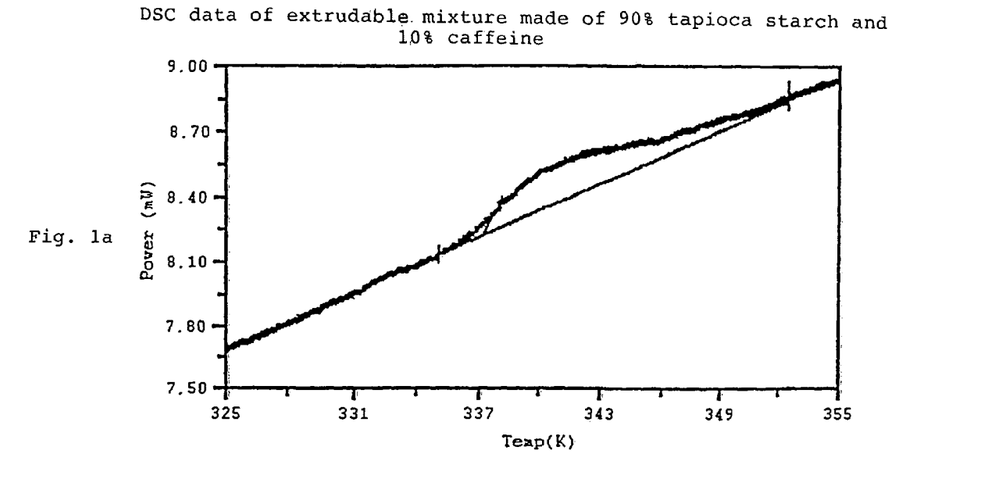
FIG. 1a shows the differential scanning colorimetry (DSC) data of an extrudable mixture made of 90% tapioca starch and 10% caffeine.

By means of differential scanning calorimetry (DSC) the transition of the crystalline or partially crystalline starch into the amorphous state can be detected. Under suitable extrusion conditions the starch becomes completely vitrified, i.e. changes into the amorphous state. By way of example, a test with tapioca starch as the polysaccharide and caffeine as the active agent was carried out. The thermogram of the pre-blend is shown in FIG. 1a, consisting of 90% tapioca starch and 10% caffeine with the addition of water, shows the typical endothermic peaks in the range of about 65° C.

Figure 1B:
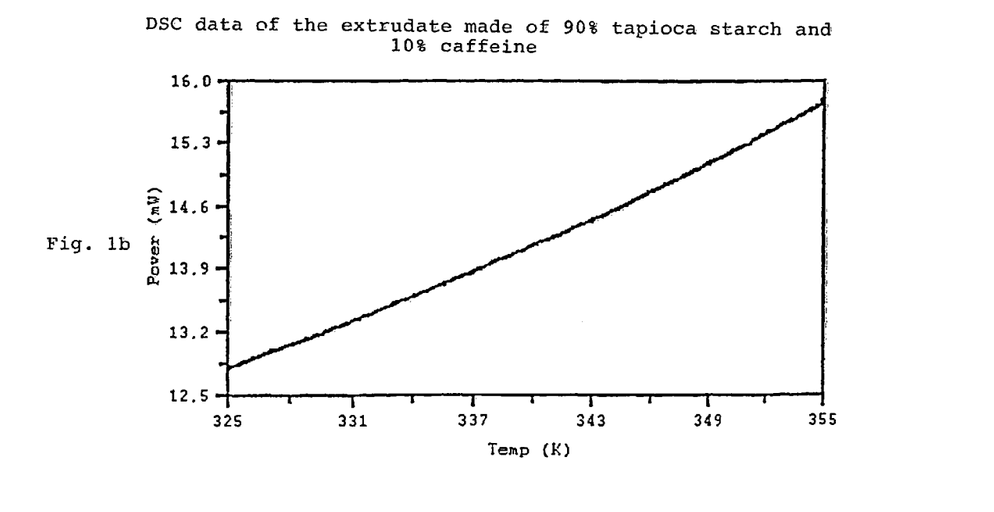
FIG. 1b shows the DSC data of an extrudate made of 90% tapioca starch and 10% caffeine.

After the extrusion carried out according to the invention, no peaks in the decisive temperature range are detectable. It has to be concluded that the starch has been completely vitrified, which means that it has turned into the amorphous state (see FIG. 1b).

Figure 2:
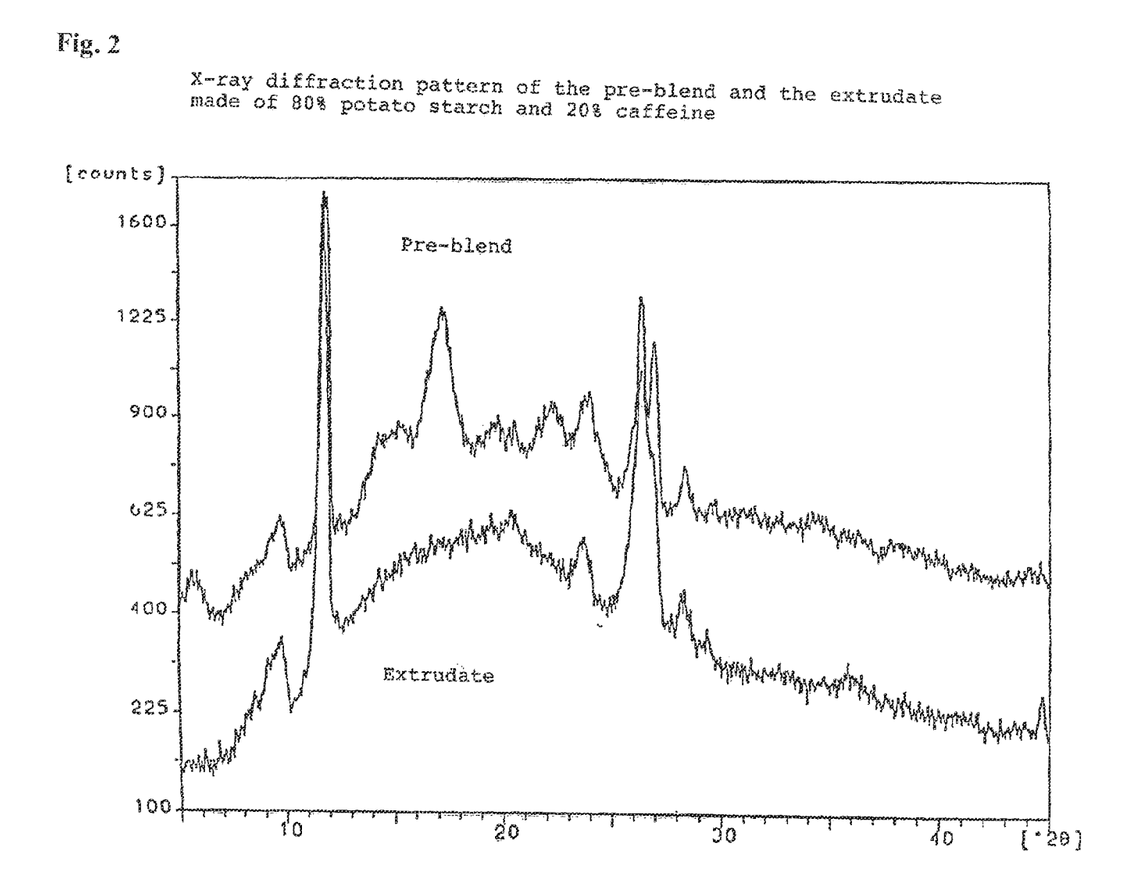
FIG. 2 shows the X-ray diffraction pattern of a pre-blend and an extrudate made of 80% potato starch and 20% caffeine.

The transition from crystalline or partially crystalline into the amorphous or partially amorphous state may also be detected with the aid of x-ray diffraction. For the following exemplary test, a sample consisting of 80% potato starch and 20 caffeine was used. The x-ray diffraction pattern of the potato starch-caffeine pre-blend shown in FIG. 2 shows the signals of the crystalline part of the starch in the range of around 20°. After application of the inventive method, the x-ray diffraction pattern of the corresponding extrudate does not have any signals anymore, which indicates a crystalline portion of the starch.

Figure 3:
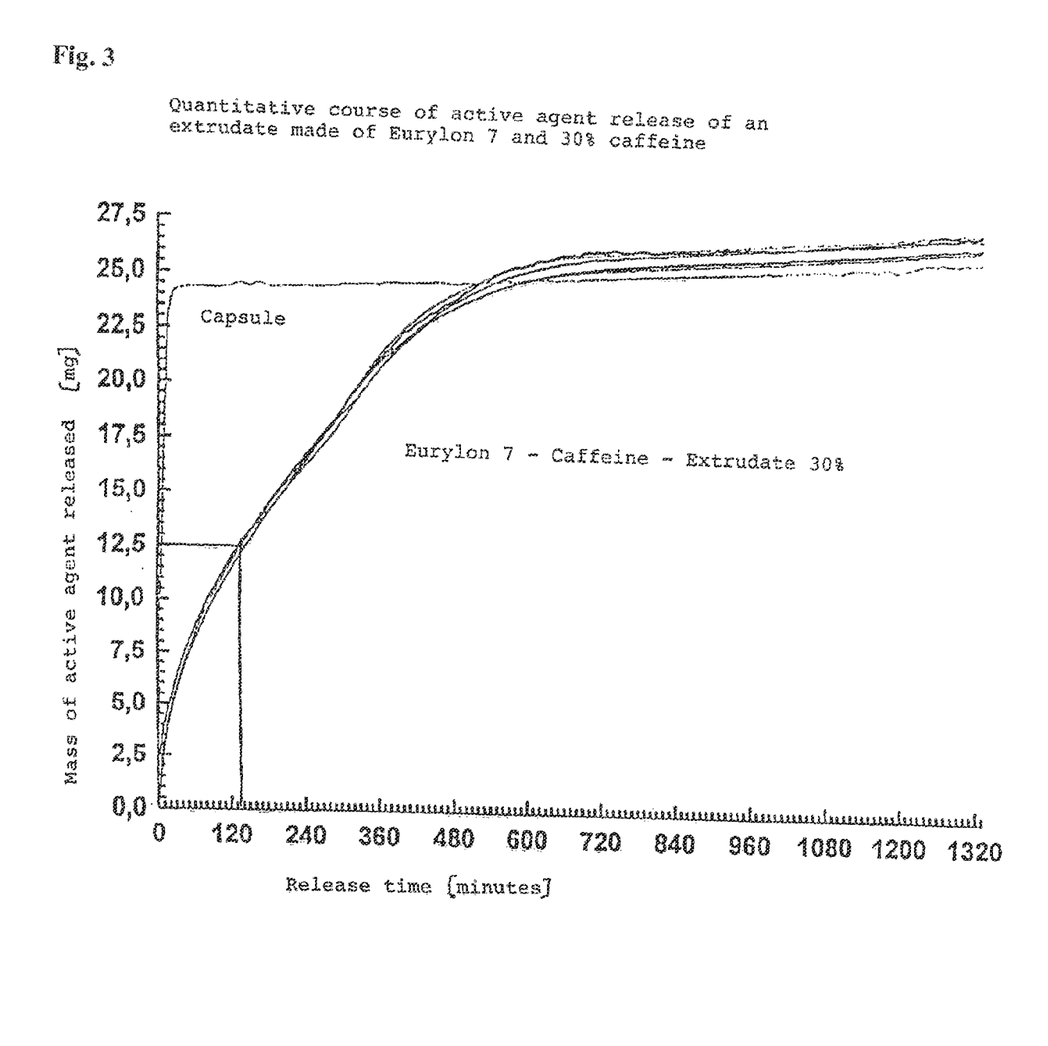
FIG. 3 shows the quantitative course of the active agent release of an extrudate made of Eurylon 7® and 30% caffeine.

In this context it is once again pointed out that the degree of destructurization into the glass state is decisive for the kinetics of the release of the active agents. Checking of the release of the active agent was done in a paddle agitator model according to USP in the liquids of 0.1 N hydrochloric acid (artificial gastric fluid having a pH value of 1) and in phosphate buffer pH 7.2 (artificial intestinal fluid). In this context it has again to be pointed out that the extrudates did not dissolve in the test, but merely a swelling of the extrudes was observed. In the following exemplary test to determine the quantitative release of the active agent, a sample consisting of a commercially available starch Eurylon 7® (amylo corn starch available from Roquette) and a 30% portion of caffeine was used. The diagram in FIG. 3 shows the quantitative course of the release of the active agent. For comparative purposes, the release of pure caffeine, not retarded and filled in a capsule has been drawn in.

One can see that embedding the caffeine in a polysaccharide matrix leads to a substantial delay in release, in the present case from about 15 minutes to about 8 to 10 hours for the total dose of 25 mg.

Figure 4:
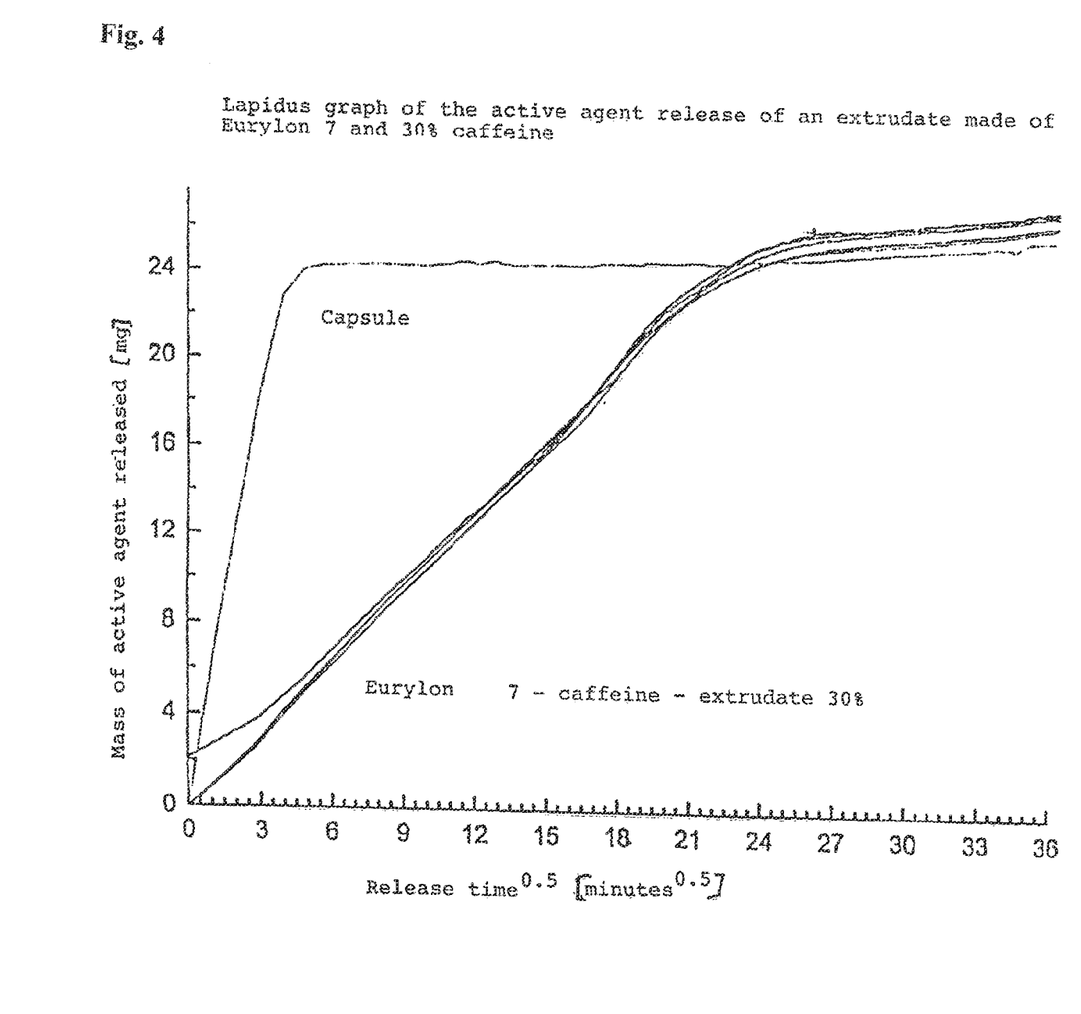
FIG. 4 shows the Lapidus graph of the active agent release of an extrudate made of Eurylon 7® and 30% caffeine.

A diagram of the amount released against the square root of time according to the lapidus rule shows an almost straight lined course of the curves, which indicates that the release of the active agent is controlled by diffusion (see FIG. 4).

Figure 5:
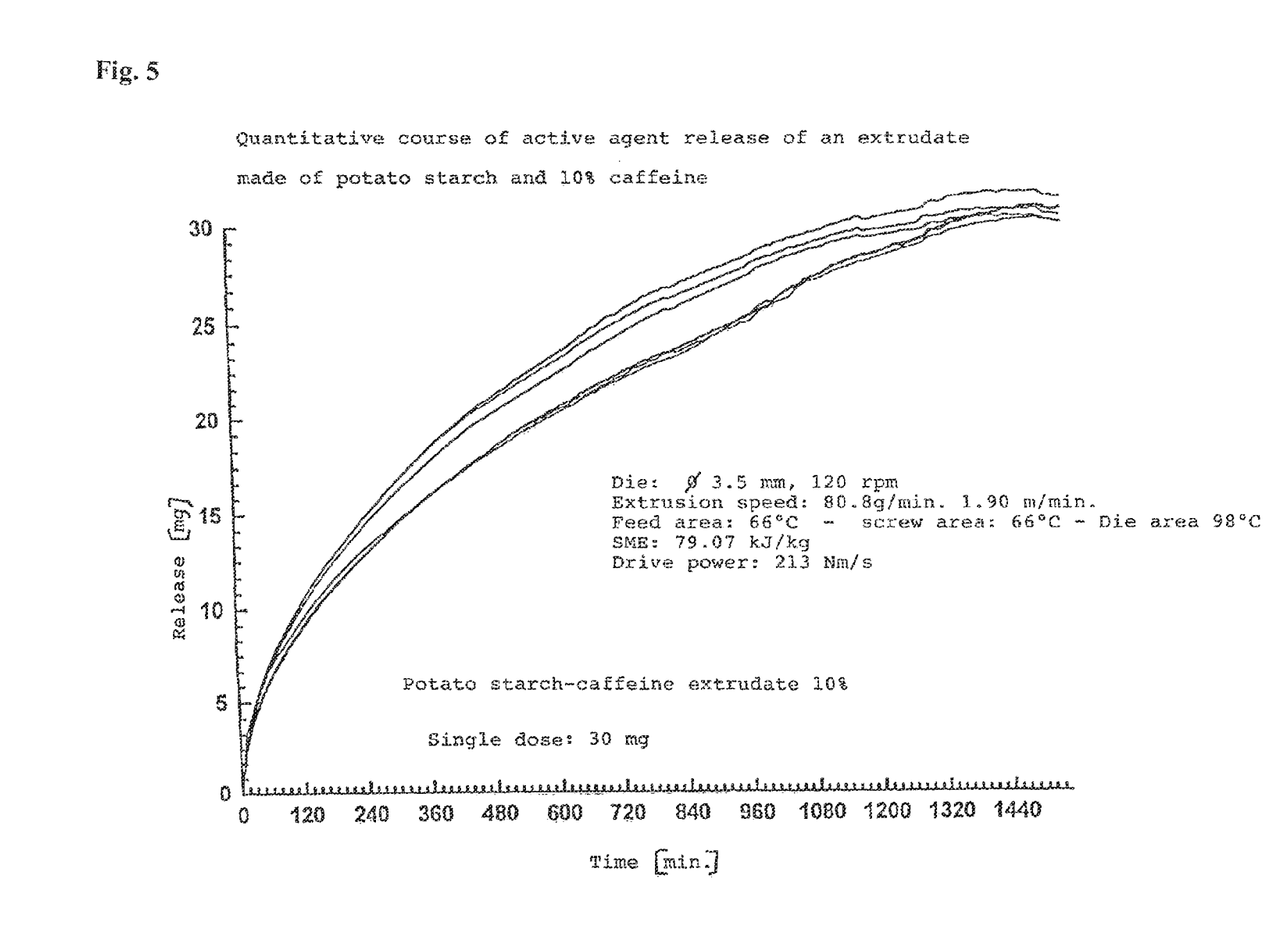
FIG. 5 shows the quantitative course of the active agent release of an extrudate made of potato starch and 10% caffeine.

As already described, the release rate of the active agent may also be regulated by the kind of polysaccharide or the polysaccharide mixture. In the following example, a pre-blend consisting of potato starch and 10% caffeine was used for a quantitative investigation of the release of the active agent. Changing the type of starch, together with a lower dose of the active agent leads to a significant slowdown in the release of the active agent. The diagram shown in FIG. 5 indicates that the extrudate prepared according to the inventive method provides a release of the active agent over a period of 24 hours.

Figure 6:
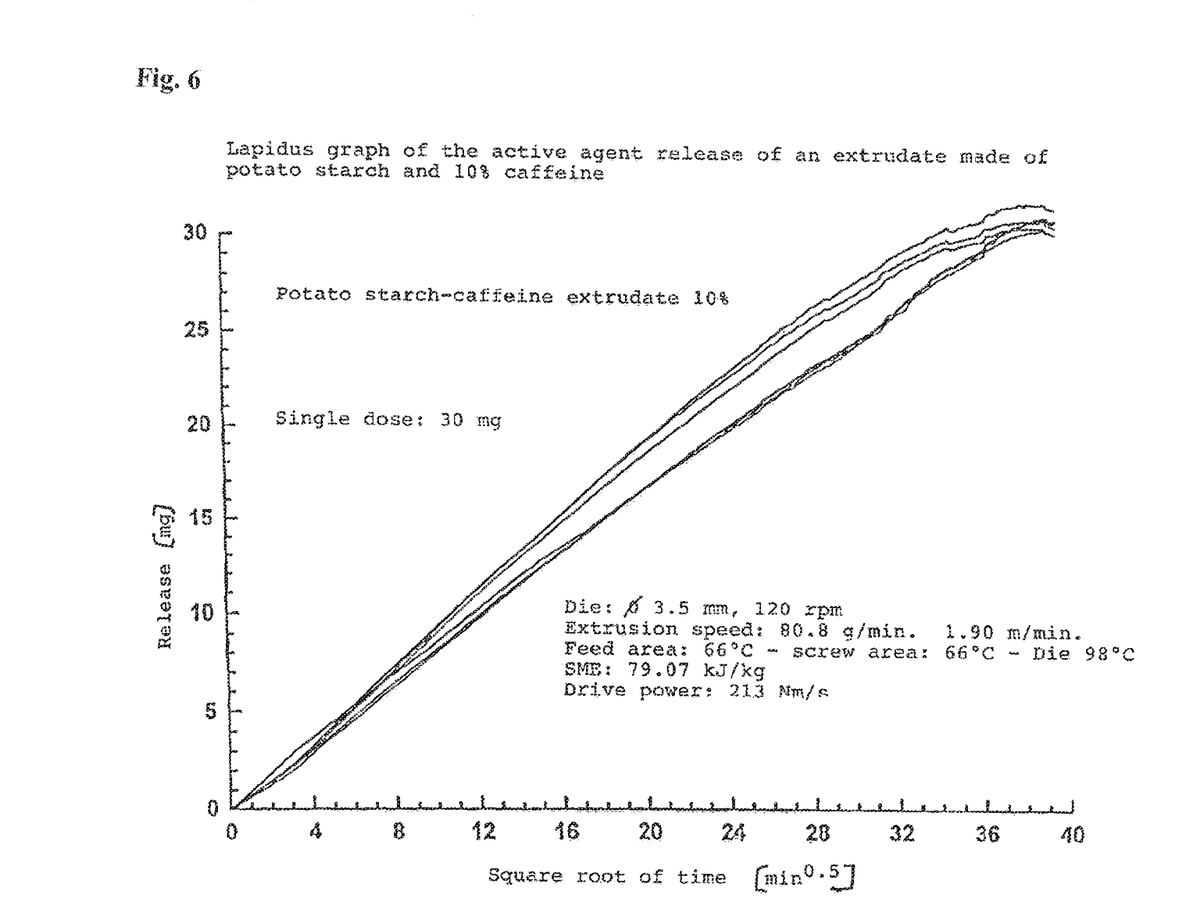
FIG. 6 shows the Lapidus graph of the active agent release of an extrudate made of potato starch and 10% caffeine.

The graph shown in FIG. 6 according to lapidus rule indicates that the release of the active agent is controlled by diffusion.

As already described above, the duration and course of the total release of the active agent can be regulated. Very long active agent release times, such as 24 hours in the above-mentioned example, are regarded as advantageous in view of the development of a new retardation principle, since in such a way "reserves" for extremely good water-soluble active agents are obtained. Release of the active agent may be selectively influenced, as already described several times, by the polysaccharides or corresponding derivatives and mixtures thereof, by the addition of corresponding adjuvants and/or by the extrusion process parameters.

According to the inventive method, faster release times of the active agents may also be achieved. The table shown below shows by way of example that a process parameter change, which for example leads to an incomplete vitrification, results in the possibility of regulating the release times of the active agent over a wide range.

TABLE

| Polysachharide | Active agent | Concentration of active agent | Period in which 50% of the active agent is released [min] | Period in which the active agent is theoretically released [hours] |
|---|---|---|---|---|
| Tapioca starch | Caffeine | 10% (50 mg) | 240 | 16 |
| Tapioca starch | Caffeine | 10% (50 mg) | 120 | 8 |
| Corn starch | Caffeine | 30% (50 mg) | 195 | 13 |
| Corn starch | Caffeine | 30% (50 mg) | 55 | 3.7 |

As can be seen from this table, for identical types of starch relatively short release times of the active agent as well as release times of the active agent falling into the range of controlled release dosage forms may be achieved solely by varying the process parameters.

The invention claimed is:

1. A method for producing a controlled release matrix, comprising co-extruding through an extruder a composition comprising a dry mixture of at least one pharmaceutically active agent and at least one starch, wherein the temperature at the orifice of the extruder during the extrusion process is below 100° C. under normal pressure, and wherein the co-extruding is under sheer force, temperature and pressure conditions such that the starch in the extruded controlled release matrix is vitrified, and wherein up to 15% by weight water is added to the composition prior to co-extruding.

2. The method of claim 1, wherein the matrix is water-insoluble.

3. The method of claim 1, wherein the co-extruding is under shear force, temperature, and pressure conditions to achieve glass transition of the starch.

4. The method of claim 1, further comprising processing the matrix into granulates or into a mono-block pharmaceutical dosage form.

5. The method of claim 1, wherein the temperature in the feed area of the extruder is about 65° C., the temperature in the screw area is about 80° C., and the temperature in the die is about 98° C.

6. The method of claim 1, wherein the starch is selected from the group consisting of tapioca starch, wheat starch, potato starch, corn starch, acetylic starch, partially pregelatinized starch, wax corn starch, amylo corn starch, and a mixture of any of the foregoing.

7. A controlled release matrix produced by the method of claim 1, 2, 4, 5 or 6.

8. The matrix of claim 7, wherein the release of the pharmaceutically active agent from the matrix substantially follows the lapidus rule.

9. The matrix of claim 7, wherein the release of the pharmaceutically active agent from the matrix is over 24 hours or more.

10. The matrix of claim 7, wherein the pharmaceutically active agent is present in the matrix as a liquid.

11. The matrix of claim 7, wherein the pharmaceutically active agent is present in the matrix as a solid.

12. The matrix of claim 7, wherein the pharmaceutically active agent is dissolved in the matrix.

13. A controlled release matrix, comprising at least one starch and at least one pharmaceutically active agent, wherein the starch in the matrix is vitrified, and wherein the starch and pharmaceutically active agent were co-extruded.

14. The matrix of claim 13, wherein the matrix is free of pores.

15. The matrix of claim 13, which is water-insoluble.

16. The matrix of claim 13, wherein the pharmaceutically active agent is present in the matrix as a liquid.

17. The matrix of claim 13, wherein the pharmaceutically active agent is present in the matrix as a solid.

18. The matrix of claim 13, wherein the pharmaceutically active agent is dissolved in the matrix.

19. The matrix of claim 13, wherein the release of the pharmaceutically active agent from the matrix substantially follows the lapidus rule.

20. The matrix of claim 13, wherein the release of the pharmaceutically active agent from the matrix is over 24 hours or more.

* * * * *